United States Patent
Ren et al.

(10) Patent No.: US 12,297,300 B2
(45) Date of Patent: May 13, 2025

(54) HYALURONIC ACID-BASED ZWITTERIONIC POLYMER BRUSH, PREPARATION METHOD THEREOF, AND USE THEREOF

(71) Applicant: South China University of Technology, Guangzhou (CN)

(72) Inventors: Li Ren, Guangzhou (CN); Sa Liu, Guangzhou (CN); Renjian Xie, Guangzhou (CN)

(73) Assignee: South China University of Technology, Guangdong (CN)

( * ) Notice: Subject to any disclaimer, the term of this patent is extended or adjusted under 35 U.S.C. 154(b) by 872 days.

(21) Appl. No.: 17/256,387

(22) PCT Filed: Dec. 12, 2018

(86) PCT No.: PCT/CN2018/120505
§ 371 (c)(1),
(2) Date: Dec. 28, 2020

(87) PCT Pub. No.: WO2020/000916
PCT Pub. Date: Jan. 2, 2020

(65) Prior Publication Data
US 2021/0147583 A1   May 20, 2021

(30) Foreign Application Priority Data
Jun. 28, 2018   (CN) .......................... 201810687134.3

(51) Int. Cl.
*C08B 37/08*   (2006.01)
*A61K 31/728*   (2006.01)
(Continued)

(52) U.S. Cl.
CPC ........ *C08B 37/0072* (2013.01); *A61K 31/728* (2013.01); *A61L 31/042* (2013.01);
(Continued)

(58) Field of Classification Search
CPC ...... C08B 37/0072; C08F 130/02; C08L 5/08; C08G 81/024; A61L 27/20; A61L 2400/10; A61L 2430/06; A61L 2430/24
See application file for complete search history.

(56) References Cited

U.S. PATENT DOCUMENTS

| | | |
|---|---|---|
| 9,561,309 B2 | 2/2017 | Glauser et al. |
| 2012/0237610 A1 | 9/2012 | Thorel et al. |
| 2014/0199349 A1 | 7/2014 | Yang et al. |

FOREIGN PATENT DOCUMENTS

| | | |
|---|---|---|
| CN | 102630157 A | 8/2012 |
| CN | 103319626 A | 9/2013 |

(Continued)

OTHER PUBLICATIONS

Chen, Meng, et al. "Lubrication at physiological pressures by polyzwitterionic brushes." science 323.5922 (2009): 1698-1701. (Year: 2009).*

(Continued)

*Primary Examiner* — Abigail Vanhorn
(74) *Attorney, Agent, or Firm* — The Webb Law Firm

(57) ABSTRACT

Disclosed are a hyaluronic acid-based zwitterionic polymer brush, a preparation method thereof, and the use thereof. The structure of the zwitterionic polymer brush is represented by formula (I), wherein n is an integer from 60-150, x is an integer from 589-686, and y is an integer from 125-230. The above-mentioned zwitterionic polymer brush can delay the pathological progress of osteoarthritis, promote cartilage regeneration, and even treat osteoarthritis and improve conditions such as the generation of abraded fragments of implants such as joints and related diseases triggered thereby, and can be combined with cartilage repairing materials to improve the frictional mechanical properties thereof for achieving better repair results. Moreover, the above-mentioned zwitterionic polymer brush can selectively bind to proteins in cartilage and has an excellent lubricating effect. The present invention has the advantages of simple method, convenient operation, easy purification, high yield, and the like.

5 Claims, 3 Drawing Sheets

(51) Int. Cl.
- A61L 27/20 (2006.01)
- A61L 31/04 (2006.01)
- A61P 19/02 (2006.01)
- C08F 130/02 (2006.01)
- C08G 81/02 (2006.01)
- C08L 5/08 (2006.01)

(52) U.S. Cl.
CPC .......... *A61P 19/02* (2018.01); *C08F 130/02* (2013.01); *C08G 81/025* (2013.01)

(56) References Cited

FOREIGN PATENT DOCUMENTS

| CN | 104140541 A | | 11/2014 |
|---|---|---|---|
| CN | 105085817 A | * | 11/2015 |
| WO | 2005118018 A1 | | 12/2005 |

OTHER PUBLICATIONS

Menaa, F., A. Menaa, and B. Menaa. "Hyaluronic acid and derivatives for tissue engineering." J Biotechnol Biomater S 3 (2011): 1. (Year: 2011).*

Ishihara et al., Why do phospholipid polymers reduce protein adsorption?. J. Biomed. Mater. Res., 39: 323-330. (Year: 1998).*

Sibarani, James, Madoka Takai, and Kazuhiko Ishihara. "Surface modification on microfluidic devices with 2-methacryloyloxyethyl phosphorylcholine polymers for reducing unfavorable protein adsorption." Colloids and Surfaces B: Biointerfaces 54.1 (2007): 88-93. (Year: 2007).*

Mäkelä, J. T. A., et al. "Functional effects of an interpenetrating polymer network on articular cartilage mechanical properties." Osteoarthritis and Cartilage 26.3 (2018): 414-421. (Year: 2018).*

Tan, Qing-Tian, Zhen-Hua Tian, and Guo-Ying Li. "Specific interaction study in collagen/hyaluronic acid blends by two-dimensional infrared correlation spectroscopy." Spectroscopy and Spectral Analysis 31.4 (2011): 970-974. (Year: 2011).*

Huang et al., A brief introduction to complex of hyaluronic acid with phospholipid, Food and Drug, 2005, pp. 1-3, vol. 2.

Wei et al. "Progress on Surface Grafted Polymer Brushes for Biomimetic Lubrication" Acta Polymerica Sinica, 2012, pp. 1-6, vol. 10.

Goda et al., "Thiolated 2-methacryloyloxyethyl phosphorylcholine for an antifouling biosensor platform", Chem. Commun, 2013, pp. 8683-8685, vol. 49.

Sae-Ung et al., "Antifouling Stripes Prepared from Clickable Zwitterionic Copolymers", Langmuir, 2017, pp. 1-23, vol. 33, No. 28.

Yu et al., "Anti-fouling bioactive surfaces", Acta Biomaterialia, 2011, pp. 1550-1557, vol. 7.

Singh et al. "Enhanced Lubrication on Tissue and Bio, material Surfaces through Peptide-mediated Binding of Hyaluronic Acid", Nat Mater, 2014, vol. 13:10, pp. 988-995.

* cited by examiner

HYALURONIC ACID-BASED ZWITTERIONIC POLYMER BRUSH, PREPARATION METHOD THEREOF, AND USE THEREOF

CROSS-REFERENCE TO RELATED APPLICATIONS

This application is the United States national phase of International Application No. PCT/CN2018/120505 filed Dec. 12, 2018, and claims priority to Chinese Patent Application No. 201810687134.3 filed Jun. 28, 2018, the disclosures of each of which are hereby incorporated by reference in their entireties.

BACKGROUND OF THE INVENTION

Field of the Invention

The present invention belongs to the technical field of biomedicine, and in particular relates to a hyaluronic acid-based zwitterionic polymer brush, a preparation method thereof, and the use thereof in the field of biomedicine. The polymer brush of the present invention is particularly suitable for preparing medicines for delaying the progress of osteoarthritis and treating osteoarthritis, and a lubricant for improving conditions such as the generation of abraded fragments of implants such as joints and related diseases triggered thereby, and can be combined with cartilage repairing materials to improve the frictional mechanical properties thereof for achieving better repair results.

Description of Related Art

Articular cartilage is a layer of special connective tissue that wraps the ends of movable articular bones. Its main functions include shock absorption and lubrication. However, due to its avascular, nerve-free, and immunocyte-free characteristics, etc., once damaged by factors such as external mechanical stimulation, it is difficult for the articular cartilage to repair by itself, leading to the weakening or even loss of cartilage function, and further to a variety of joint diseases. The main components of natural synovial fluid include hyaluronic acid, proteins (mainly albumin and γ-globulin), lubricin, aggrecan and phospholipids. Under the action of shearing, the main components in the natural synovial fluid undergo self-assembly and assemble into a bottle-brush-like structural macromolecule with the hyaluronic acid as the main chain and the lubricin and aggrecan as a side chain; this macromolecule then binds to the surface of cartilage by means of lubricin and further assembles with the phospholipids, which can function as a boundary lubricant to effectively reduce the friction between cartilages during joint movement and ensure a healthy life for humans. Osteoarthritis, also known as degenerative osteoarthritis due to abrasion, is a typical joint disease caused by weakening of lubricating properties of cartilages due to cartilage degeneration. It has a very high incidence rate, and relevant investigations show that its incidence rate is up to 80% in individuals over 55 years old. The main clinical symptoms of osteoarthritis manifest as arthralgia, stiffness, local erosion and abrasion of cartilage, restricted movement and even severe dysfunction. Abraded fragments generated by abrasion activate pathways related to cartilage decomposition, such as the up-regulation of the secretion of matrix metalloproteinase 13 that degrades the cartilage matrix, which further accelerates the destruction and degradation of cartilage, intensifies the cartilage abrasion, produces more abraded fragments, and triggers a vicious cycle.

In order to improve the lubricating properties of cartilages, reduce the generation of cartilaginous abraded fragments and thereby delay the pathological progress of osteoarthritis, and even achieve the purpose of treating osteoarthritis, many research groups at home and abroad have carried out researches on biomimetic lubrication. However, the current researches mostly focus on the biomimetic construction of single components in joint synovial fluid, such as lubricin, aggrecan, etc. On the one hand, the function of the bottle-brush-like macromolecule formed above with the hyaluronic acid as the main chain and the lubricin or aggrecan as a side chain in achieving an excellent lubricating property in cartilages is not fully realized; on the other hand, the prepared biomimetic lubricant cannot effectively bind to the surface of cartilages or the way of binding is destructive or unstable to a certain extent. In this context, a biomimetic lubricant based on this bottle-brush-like macromolecule is designed and synthesized.

SUMMARY OF THE INVENTION

In order to overcome the above-mentioned shortcomings and deficiencies in the prior art, the primary object of the present invention is to provide a zwitterionic polymer brush based on hyaluronic acid and 2-methacryloyloxyethyl phosphorylcholine (MPC).

Another object of the present invention is to provide a preparation method for the above-mentioned zwitterionic polymer brush based on hyaluronic acid and 2-methacryloyloxyethyl phosphorylcholine.

Yet another object of the present invention is to provide the use of the above-mentioned zwitterionic polymer brush based on hyaluronic acid and 2-methacryloyloxyethyl phosphorylcholine in the field of biomedicine; particularly the use in preparing medicines for treating osteoarthritis, and/or a lubricant for improving the lubricating and frictional properties of prostheses; or in modifying cartilage repairing materials to improve frictional mechanical properties thereof.

The objects of the present invention are achieved by the following schemes:

A zwitterionic polymer brush based on hyaluronic acid and 2-methacryloyloxyethyl phosphorylcholine has the structure as shown below:

Formula I

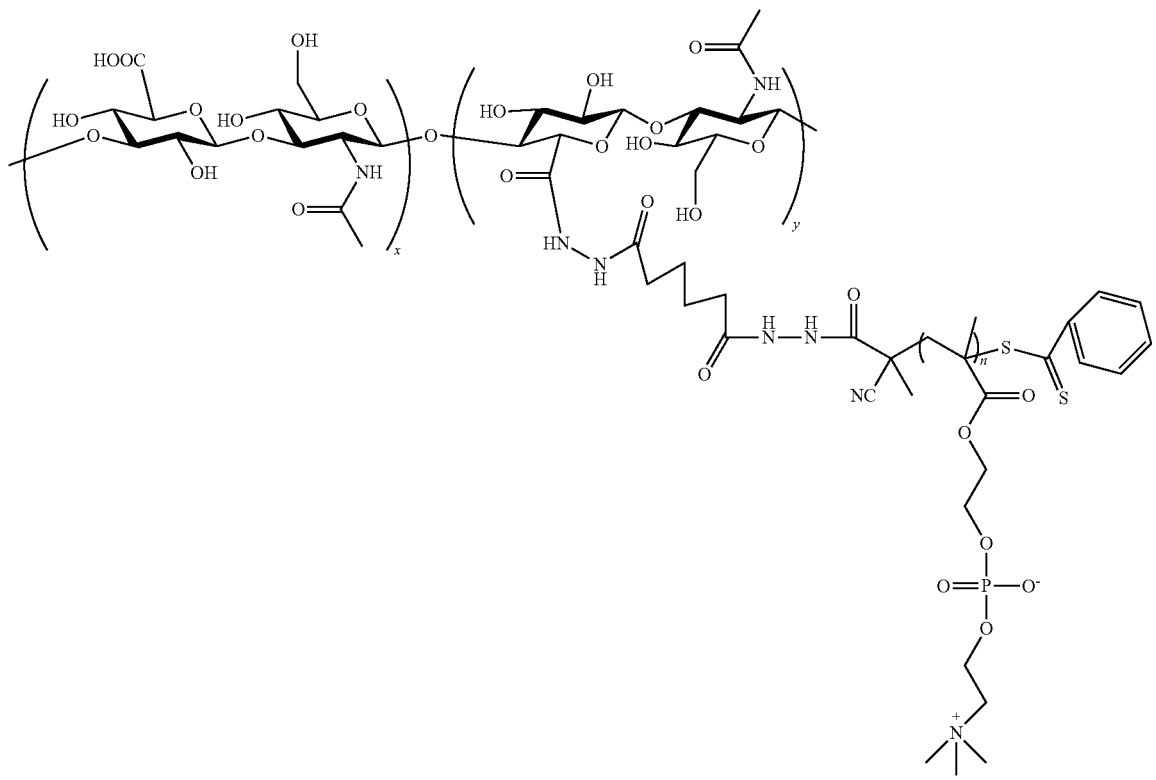

wherein n is an integer from 60-150, x is an integer from 589-686, and y is an integer from 125-230.

A preparation method for the zwitterionic polymer brush based on hyaluronic acid and 2-methacryloyloxyethyl phosphorylcholine comprises the following steps:
(1) reacting hyaluronic acid and adipic acid dihydrazide to obtain amino-modified hyaluronic acid (HA-ADH);
(2) subjecting same to reversible addition-fragmentation chain transfer radical polymerization to obtain poly(2-methacryloyloxyethyl phosphorylcholine) (PMPC) carrying a carboxyl group at the terminal under the action of an initiator and a chain transfer agent, by taking 2-methacryloyloxyethyl phosphorylcholine as a polymerization monomer; and
(3) mixing the above-mentioned amino-modified hyaluronic acid (HA-ADH), and poly(2-methacryloyloxyethyl phosphorylcholine) (PMPC) carrying a carboxyl group at the terminal with activators, and reacting same in an aqueous solution system to obtain the zwitterionic polymer brush based on hyaluronic acid and 2-methacryloyloxyethyl phosphorylcholine.

The reaction in step (1) is carried out under the action of 1-ethyl-(3-dimethylaminopropyl) carbodiimide hydrochloride;
the temperature of the reaction in step (1) is 25° C.-35° C.;
the pH of the reaction system is preferably 4.7-4.85. The reaction preferably proceeds until the pH value of the system does not change.

The amounts of the hyaluronic acid and adipic acid dihydrazide used in step (1) can be at any ratio, and the mass ratio is preferably 1:4 to 1:18.

The chain transfer agent in step (2) is preferably 4-cyano-4-(phenylcarbonothioylthio) pentanoic acid (CTP). The molar ratio of the 2-methacryloyloxyethyl phosphorylcholine (MPC) to CTP is preferably 100:1 to 200:1.

The initiator in step (2) is preferably 4,4'-azobis(4-cyanovaleric acid) (ACVA), and the molar ratio of ACVA to CTP is 1:(2-10), preferably 1:2.

The temperature of the polymerization in step (2) is 60° C.-70° C., and the polymerization time is 6-24 h.

The solvent used in the polymerization in step (2) is ethanol, water, methanol, etc., and preferably methanol is used as the solvent.

The amounts of the amino-modified hyaluronic acid and PMPC carrying a carboxyl group at the terminal used in step (3) can be at any ratio, or adjusted according to the requirements of the structural design, and the molar ratio of the amino group to the carboxyl group is preferably 1:(1.1-2).

The activators in step (3) are preferably 1-ethyl-3-[3-(dimethylamino) propyl] carbodiimide (EDC) and N-hydroxysuccinimide (NHS), and the mass ratio of the activators EDC to NHS used therein is preferably 1:1 to 1:2;
the temperature of the reaction in step (3) is 25° C.-35° C., the reaction time is 18-36 h, and more preferably the reaction condition is performed at 30° C. for 24 h.

The pH value of the reaction system in step (3) is 5-7, and preferably the pH value is 5.5-6.

The zwitterionic polymer brush based on hyaluronic acid and 2-methacryloyloxyethyl phosphorylcholine of the present invention is a biomimetic lubricant based on the bottle-brush-like macromolecule formed by the components in the natural synovial fluid assembled under the action of shearing, and has the effect of improving lubrication. It not only overcomes the shortcomings of hyaluronic acid and a biomimetic lubricant for a single synovial fluid component, but also realizes the biomimetic effect of the structure and components of the bottle-brush-like macromolecule that plays a key role in natural cartilage, thus achieving a better lubricating effect. Therefore, it can be used in the field of biomedicine. It is particularly suitable for preparing medicines for treating osteoarthritis, a lubricant for improving the lubricating and frictional properties of implanted prostheses such as joints, and can be combined with cartilage repairing materials to improve the frictional mechanical properties thereof.

The zwitterionic polymer brush of the present invention is used as a biomimetic lubricant.

Compared with the prior art, the present invention has the following advantages and beneficial effects:

(1) the preparation method for the zwitterionic polymer brush based on hyaluronic acid and 2-methacryloyloxyethyl phosphorylcholine of the present invention has the advantages of simple route, convenient operation, easy purification, high yield, and the like;

(2) the zwitterionic polymer brush based on hyaluronic acid and 2-methacryloyloxyethyl phosphorylcholine of the present invention is a biomimetic product for the bottle-brush-like macromolecule with a composite structure formed in natural joints and with hyaluronic acid as the main chain, instead of a biomimetic product for a single component, and has a better lubricating effect;

(3) the zwitterionic polymer brush based on hyaluronic acid and 2-methacryloyloxyethyl phosphorylcholine of the present invention selectively binds to the proteins in cartilage, and the way by which same binds to the cartilage is naturally harmless; and (4) the zwitterionic polymer brush based on hyaluronic acid and 2-methacryloyloxyethyl phosphorylcholine of the present invention has a better therapeutic effect than hyaluronic acid currently used clinically in slowing the pathological development of osteoarthritis.

BRIEF DESCRIPTION OF THE DRAWINGS

FIG. 1-(2) is a polymerization reaction diagram of 2-methacryloyloxyethyl phosphorylcholine; and FIG. 1-(3) is a preparation reaction diagram of the zwitterionic polymer brush.

DETAILED DESCRIPTION

The present invention will be further described in detail below in conjunction with the embodiments and accompanying drawings, but this does not limit the implementation of the present invention. The reagents in the following embodiments are all commercially available.

Figure 1:
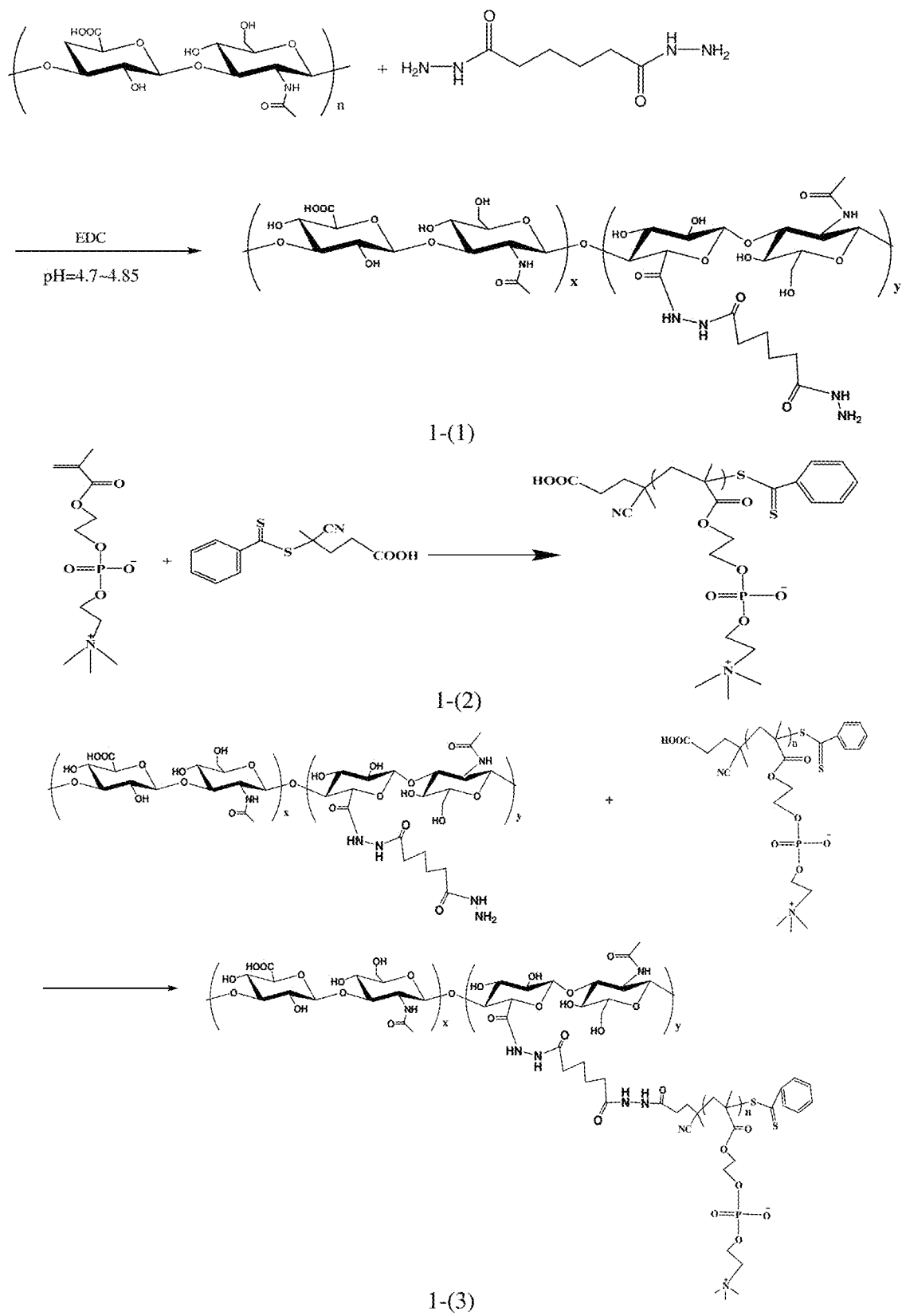
FIG. 1 is a schematic diagram of the synthetic route of the zwitterionic polymer brush, in which FIG. 1-(1) is a schematic diagram of the reaction of adipic acid dihydrazide modified hyaluronic acid.

The schematic diagram of the synthetic route of the zwitterionic polymer brush based on hyaluronic acid and 2-methacryloyloxyethyl phosphorylcholine of the present invention is as shown in FIG. 1, in which FIG. 1-(1) is a schematic diagram of the reaction of adipic acid dihydrazide modified hyaluronic acid; FIG. 1-(2) is a schematic diagram of the polymerization reaction of 2-methacryloyloxyethyl phosphorylcholine; and FIG. 1-(3) is a schematic diagram of the preparation reaction of the zwitterionic polymer brush.

Embodiment 1

Preparation of a Zwitterionic Polymer Brush Based on Hyaluronic Acid and 2-Methacryloyloxyethyl Phosphorylcholine:

(1) dissolving 100 mg of hyaluronic acid with a molecular weight of 1-1.5 million in 20 mL of deionized water, and stirring same for dissolution, so as to obtain a hyaluronic acid solution; mixing 1.736 g of adipic acid dihydrazide with the hyaluronic acid solution, the mass ratio of the adipic acid dihydrazide to hyaluronic acid being 17.36:1; adjusting the pH value of the solution to 4.75 with 1 M hydrochloric acid, and adding 0.191 g of 1-ethyl-3-[3-(dimethylamino)propyl] carbodiimide (EDC) in a solid form, to further adjust the pH value of the solution to 4.75; carrying out a reaction at 30° C. until the pH value does not change; and dialyzing and lyophilizing same to obtain the amino-modified hyaluronic acid;

(2) dissolving 10 g of 2-methacryloyloxyethyl phosphorylcholine (MPC) in 30 mL of anhydrous methanol, and weighing 37.5 mg of 4,4'-azobis(4-cyanovaleric acid) (ACVA) as the initiator, and 75 mg of 4-cyano-4-(phenylcarbonothioylthio) pentanoic acid (CTP) as the chain transfer agent, adding the initiator and the chain transfer agent to the solution of MPC in anhydrous methanol, stirring same for dissolution, then sealing same, and introducing nitrogen for oxygen removal in an ice bath for 40 minutes;

(3) placing the deoxygenated MPC solution in an oil bath preheated to 60° C. to react for 12 h, quenching the reaction via liquid nitrogen, and after returning to room temperature, precipitating same with 1 L of acetone, pouring out the supernatant, and then drying same under a vacuum at 30° C., to obtain 7.981 g of poly(2-methacryloyloxyethyl phosphorylcholine) (PMPC) carrying a carboxyl group at the terminal; and (4) taking 100 mg of the product in step (1) and 2 g of the product in step (3) and dissolving same in deionized water, adjusting the pH value of the solution to 5.5, adding 60 mg of EDC/NHS (a molar ratio of 1:1), then carrying out a reaction at 30° C., pH=5.5 for 24 h, the molar ratio of the amino group to the carboxyl group in the amino-modified hyaluronic acid and PMPC carrying a carboxyl group at the terminal being 1:1.5, after the completion of the reaction, dialyzing and lyophilizing same to obtain 154.1 mg of the zwitterionic polymer brush based on hyaluronic acid and 2-methacryloyloxyethyl phosphorylcholine.

Figure 2:
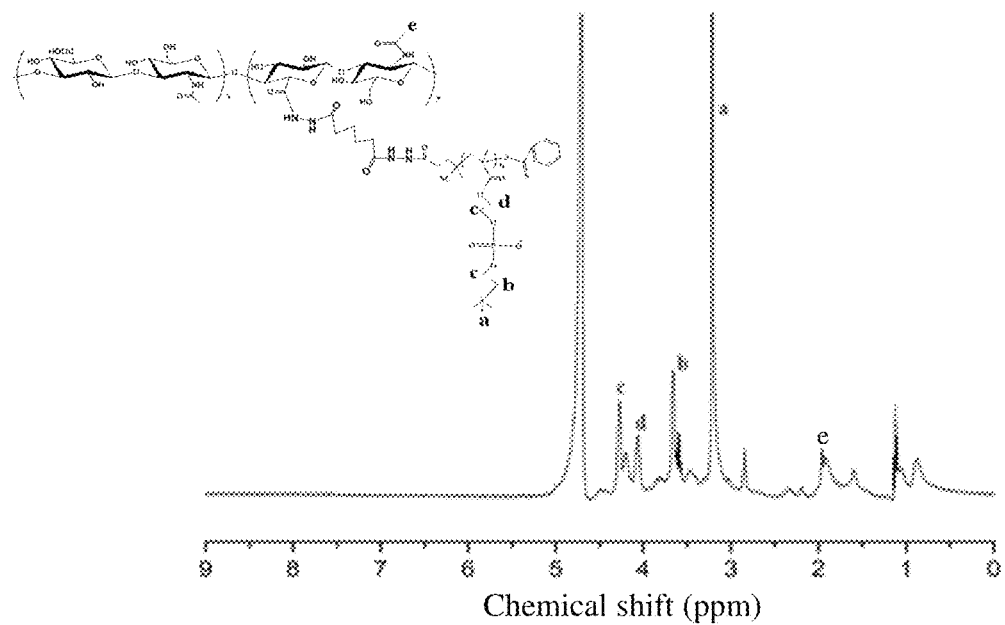
FIG. 2 shows the NMR spectrum 2-(1) and the infrared spectrum 2-(2) of the zwitterionic polymer brush obtained in Embodiment 1, wherein in the figures, HPM is the zwitterionic polymer brush, PMPC is the poly(2-methacryloyloxyethyl phosphorylcholine) carrying a carboxyl group at the terminal, and HA-ADH is the amino-modified hyaluronic acid.
Figure 2:
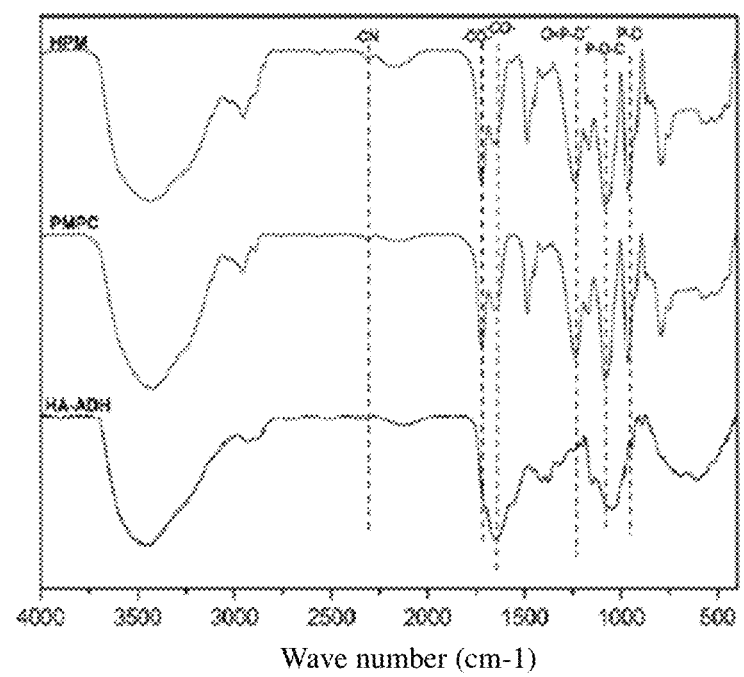

FIG. 2 shows the NMR spectrum 2-(1) and the infrared spectrum 2-(2) of the zwitterionic polymer brush obtained in Embodiment 1.

Embodiment 2

Preparation of an Anionic Polymer Brush Based on Hyaluronic Acid and 2-Acrylamido-2-Methylpropanesulfonic Acid:

(1) dissolving 100 mg of hyaluronic acid with a molecular weight of 1-1.5 million in 20 mL of deionized water, and stirring same for dissolution, so as to obtain a hyaluronic acid solution; mixing 435.4 mg of adipic acid dihydrazide with the hyaluronic acid solution, the mass ratio of the adipic acid dihydrazide to hyaluronic acid being 4.35:1; adjusting the pH value of the solution to 4.8 with 1 M hydrochloric acid, and adding 30 mg of 1-ethyl-3-[3-(dimethylamino)propyl]carbodiimide (EDC) in a solid form, to further adjust the pH value of the solution to 4.8; carrying out a reaction at 30° C. until the pH value does not change; and dialyzing and lyophilizing same to obtain the amino-modified hyaluronic acid;

(2) dissolving 2 g of 2-methacryloyloxyethyl phosphorylcholine (MPC) in 6 mL of anhydrous methanol, and weighing 7.5 mg of 4,4'-azobis(4-cyanovaleric acid) (ACVA) as the initiator, and 15 mg of 4-cyano-4-(phenylcarbonothioylthio) pentanoic acid (CTP) as the chain transfer agent, adding the initiator and the chain transfer agent to the solution of MPC in anhydrous methanol, stirring same for dissolution, then sealing same, and introducing nitrogen for oxygen removal in an ice bath for 30 minutes;

(3) placing the deoxygenated MPC solution in an oil bath preheated to 60° C. to react for 12 h, quenching the reaction via liquid nitrogen, and after returning to room temperature, precipitating same with 300 mL of acetone, pouring out the supernatant, and then drying same under a vacuum at 30° C., to obtain 1.535 g of poly(2-methacryloyloxyethyl phosphorylcholine) (PMPC) carrying a carboxyl group at the terminal; and (4) taking 50 mg of the product in step (1) and 1 g of the product in step (3) and dissolving same in deionized water, adjusting the pH value of the solution to 5.5, adding 60 mg of EDC/NHS (a molar ratio of 1:1), then carrying out a reaction at 30° C., pH=5.5 for 24 h, the molar ratio of the amino group to the carboxyl group in the amino-modified hyaluronic acid and PMPC carrying a carboxyl group at the terminal being 1:1.5, after the completion of the reaction, dialyzing and lyophilizing same to obtain 83.5 mg of the zwitterionic polymer brush based on hyaluronic acid and 2-methacryloyloxyethyl phosphorylcholine.

Embodiment 3

Preparation of an Anionic Polymer Brush Based on Hyaluronic Acid and 2-Acrylamido-2-Methylpropanesulfonic Acid:

(1) dissolving 100 mg of hyaluronic acid with a molecular weight of 1-1.5 million in 20 mL of deionized water, and stirring same for dissolution, so as to obtain a hyaluronic acid solution; mixing 868 mg of adipic acid dihydrazide with the hyaluronic acid solution, the mass ratio of the adipic acid dihydrazide to hyaluronic acid being 8.68:1; adjusting the pH value of the solution to 4.8 with 1 M hydrochloric acid, and adding 60 mg of 1-ethyl-3-[3-(dimethylamino)propyl]carbodiimide (EDC) in a solid form, to further adjust the pH value of the solution to 4.8; carrying out a reaction at 30° C. until the pH value does not change; and dialyzing and lyophilizing same to obtain the amino-modified hyaluronic acid;

(2) dissolving 5 g of 2-methacryloyloxyethyl phosphorylcholine (MPC) in 15 mL of anhydrous methanol, and weighing 19 mg of 4,4'-azobis(4-cyanovaleric acid) (ACVA) as the initiator, and 38 mg of 4-cyano-4-(phenylcarbonothioylthio)pentanoic acid (CTP) as the chain transfer agent, adding the initiator and the chain transfer agent to the solution of MPC in anhydrous methanol, stirring same for dissolution, then sealing same, and introducing nitrogen for oxygen removal in an ice bath for 30 minutes;

(3) placing the deoxygenated MPC solution in an oil bath preheated to 60° C. to react for 12 h, quenching the reaction via liquid nitrogen, and after returning to room temperature, precipitating same with 600 mL of acetone, pouring out the supernatant, and then drying same under a vacuum at 30° C., to obtain 3.643 g of poly(2-methacryloyloxyethyl phosphorylcholine) (PMPC) carrying a carboxyl group at the terminal; and (4) taking 150 mg of the product in step (1) and 3 g of the product in step (3) and dissolving same in deionized water, adjusting the pH value of the solution to 5.5, adding 60 mg of EDC/NHS (a molar ratio of 1:1), then carrying out a reaction at 30° C., pH=5.5 for 24 h, the molar ratio of the amino group to the carboxyl group in the amino-modified hyaluronic acid and PMPC carrying a carboxyl group at the terminal being 1:1.5, after the completion of the reaction, dialyzing and lyophilizing same to obtain 201 mg of the zwitterionic polymer brush based on hyaluronic acid and 2-methacryloyloxyethyl phosphorylcholine.

Embodiment 4

Testing of the lubricating property of the polymer brush prepared in Embodiment 1 using a Bruker frictional abrasion testing machine. The specific method is as follows:

(1) formulating a solution of polymer brush in PBS with a concentration of 0.2 mg/mL, and a solution of hyaluronic acid in PBS with a concentration of 1 mg/mL; and (2) taking fresh pig joints, removing the articular cartilage (avoiding any damage to the cartilage), cutting the cartilage into a size of about 1.5 cm×1 cm, at the same time using a trephine to take a cartilage nail with a diameter of 6 mm, and treating same with 0.5% pancreatin for 3 h, then washing same with serum to imitate cartilage with osteoarthritic lesions, selecting a cartilage sheet with a flat surface and fixing same on a pathological grade glass slide, and then fixing the pathological grade glass slide with immobilized cartilage to a petri dish with a diameter of 10 mm, the cartilage nails being fixed by the built-in fixture of the frictional abrasion testing machine. Subsequently, 0.2 mg/mL of the solution of polymer brush in PBS, 1 mg/mL of the solution of hyaluronic acid in PBS and a natural bovine synovial fluid are added to measure the friction coefficient under different lubrication media, and the measurement is repeated 3 times. The results are summarized in FIG. 3.

Figure 3:
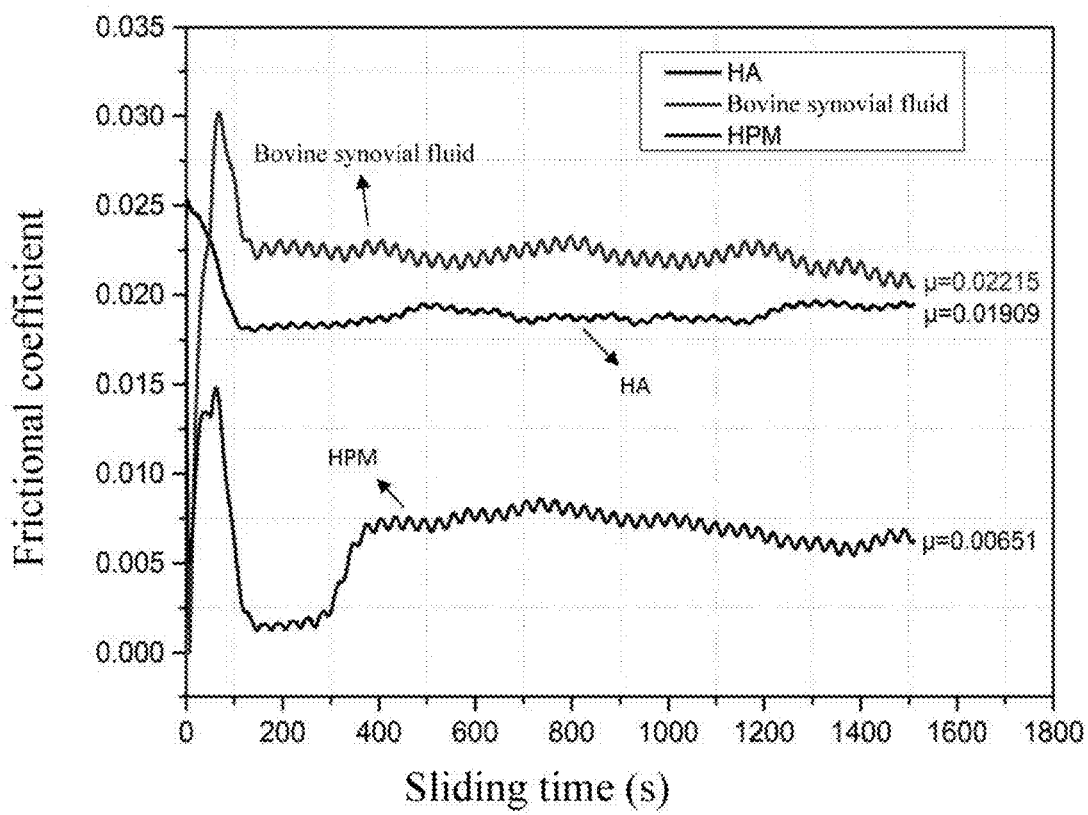
FIG. 3 shows the lubricating effect of the zwitterionic polymer brush obtained in Embodiment 1, wherein HPM is the zwitterionic polymer brush, and HA is hyaluronic acid.

It can be seen from FIG. 3 that compared with hyaluronic acid and natural bovine synovial fluid, the zwitterionic polymer brush based on hyaluronic acid and 2-methacryloyloxyethyl phosphorylcholine has a better lubricating effect, and the friction coefficient significantly decreases.

Embodiment 5

Evaluation of the effect of the polymer brush prepared in Embodiment 1 on delaying the progress of osteoarthritis using a rat osteoarthritis model. The specific method is as follows:

taking 24 SPF grade SD rats, which are male and 4 months old; after passing the quarantine inspection, anesthetizing all animals with zoletil (40 mg/kg) and xylazine (10 mg/kg), opening the rat's right knee joint capsule and cutting the anterior cruciate ligament with a scalpel; randomly dividing the rats for which a model was successfully established and which survived into 4 groups of A, B, C, and D, with 6 rats per group; performing intra-articular injection into the animals' right knee at day 14, day 21, day 35 and day 42 of rearing after the operation, wherein the rats in group A were not treated and used as a blank control group, the rats in group B were injected with 100 μL of PBS into the articular cavity, the rats in group C were injected with 100 μL of hyaluronic acid solution into the articular cavity, and the rats in group D were injected with 100 μL of a solution of the zwitterionic polymer brush (HPM) based on hyaluronic acid and 2-methacryloyloxyethyl phosphorylcholine into the articular cavity.

Testing:
(1) observing and recording the general clinical conditions of the animals every day, and measuring the animals' body weight once a week;
(2) on day 49 after the operation, sacrificing the rats and taking out their articular cartilage, taking the articular cartilage from the left untreated joint of all the animals, and taking the left articular cartilage of 3 animals as the reference groups;
(3) decalcifying and dehydrating the obtained rat joints, cutting out 15 μm×15 μm cartilage samples, embedding same in paraffin, and then staining same with toluidine blue and safranin O; and staining type II collagen with an anti-col 2A1 monoclonal antibody.

Figure 4:
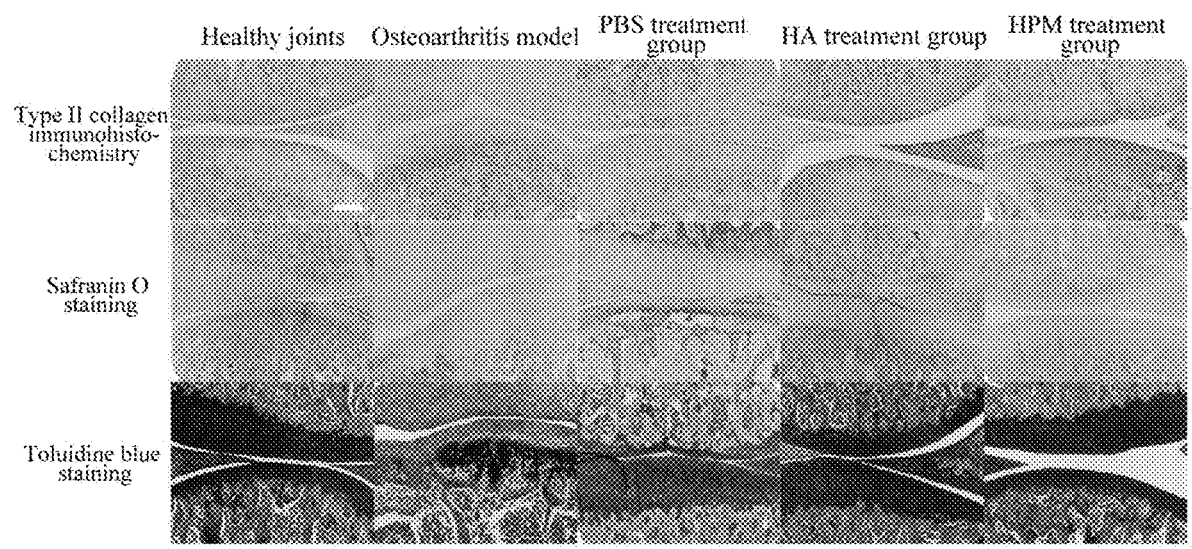
FIG. 4 shows a diagram of the effect of the zwitterionic polymer brush obtained in Embodiment 1 on slowing osteoarthritis (scale: 500 μm).

The results are summarized in FIG. 4.

It can be seen from FIG. 4 that the articular cartilage is obviously thinned during rearing after the anterior cruciate ligament of the SD rats is removed, the surface of the cartilage is rough, uneven, and discontinuous, and local cartilage detaches, showing obvious symptoms of osteoarthritis, and indicating that the osteoarthritis model is successfully established, while the surface of the articular cartilage of healthy rats is flat and smooth. Compared with the hyaluronic acid and PBS treatment groups, the roughness and unevenness of the cartilage surface in the HPM treatment group are significantly improved, and the OARSI score is also significantly reduced, indicating that under the action of HPM, abrasion and degradation of cartilage are effectively improved, which thus effectively slows the pathological progress of osteoarthritis.

Embodiment 6

Investigation of the interaction of the polymer brush (HPM) prepared in Embodiment 1 with synovial fluid and proteins in cartilage using a VP-ITC isothermal calorimetric titrator (MICROCAL, USA). The specific method is as follows:

(1) formulating 0.2 mg/mL of a solution of HPM in PBS and 0.2 mg/mL of an acetic acid solution (the concentration of acetic acid being 5 mg/mL), 7 mg/mL and 11 mg/mL of solutions of albumin and γ-globulin in PBS, 0.5 mg/mL of a type II collagen solution (5 mg/mL of acetic acid as a solvent), and 0.5 mg/mL of a fibronectin solution (PBS as a solvent);
(2) titrating the blank curves of the solvent PBS and 5 mg/mL of acetic acid using a VP-ITC isothermal calorimetric titrator, as the experimental backgrounds;
(3) titrating the interaction curves of HPM and various proteins, separately, and obtaining the binding constants of the interaction between HPM and various proteins after subtracting the experimental background corresponding to the previous step.

The results are summarized in Table 1. As shown in Table 1, the binding constants of HPM with albumin, globulin, fibronectin and type II collagen vary greatly, wherein the binding constants with type II collagen and fibronectin have an order of magnitude difference from the binding constants with albumin and globulin, showing a selective interaction with the proteins, such that HPM can selectively bind to the proteins in cartilage, and the way by which same binds to the cartilage is naturally harmless. While hyaluronic acid does not show such selectivity. (HA is hyaluronic acid)

TABLE 1

Binding constants of zwitterionic polymer brush with major proteins in synovial fluid and cartilage

| | Fibronectin | Type II collagen | γ-globulin | Albumin |
|---|---|---|---|---|
| HA | 0.072 | 1.17 | 3220 | 9040 |
| HPM | $8.15 \times 10^6$ | $4.46 \times 10^6$ | 265 | 70.3 |

The above-mentioned embodiments are preferred embodiments of the present invention, but the embodiments of the present invention are not limited to the above-mentioned embodiments, and any other changes, modifications, substitutions, combinations and simplifications made without departing from the spirit and principle of the present invention should all be equivalent replacement methods and should all be included in the scope of protection of the present invention.

The invention claimed is:

1. A zwitterionic polymer brush based on hyaluronic acid and 2-methacryloyloxyethyl phosphorylcholine, comprising the following structure capable of binding to fibronectin and type II collagen in cartilage:

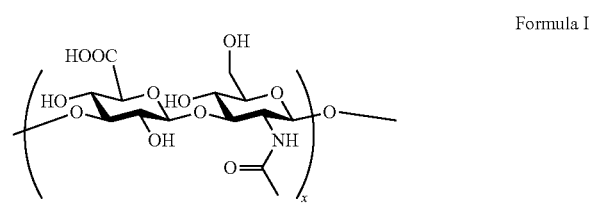

Formula I

-continued

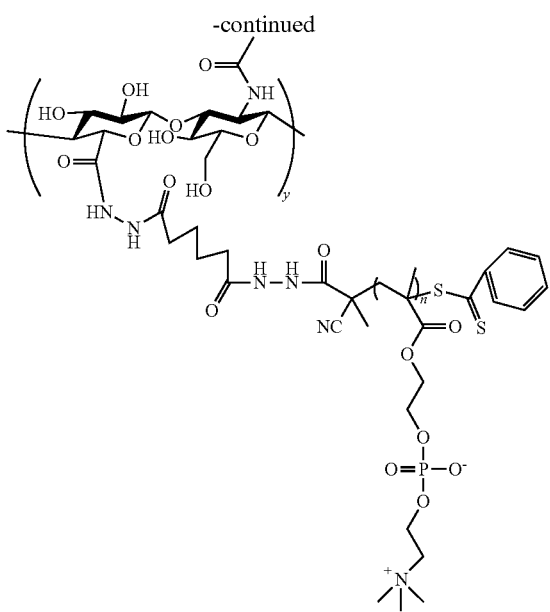

wherein n is an integer from 60-150, x is an integer from 589-686, and y is an integer from 125-230.

2. A biomedicine comprising the zwitterionic polymer brush based on hyaluronic acid and 2-methacryloyloxyethyl phosphorylcholine according to claim 1.

3. A medicine for treating osteoarthritis comprising the zwitterionic polymer brush based on hyaluronic acid and 2-methacryloyloxyethyl phosphorylcholine according to claim 1, and combining with cartilage repairing materials to improve the frictional mechanical properties thereof.

4. A lubricant for improving the lubricating and frictional properties of implanted prostheses comprising the zwitterionic polymer brush based on hyaluronic acid and 2-methacryloyloxyethyl phosphorylcholine according to claim 1, and combining with cartilage repairing materials to improve the frictional mechanical properties thereof.

5. A biomimetic lubricant for improving the frictional property of cartilage repairing materials comprising the zwitterionic polymer brush based on hyaluronic acid and 2-methacryloyloxyethyl phosphorylcholine according to claim 1.

* * * * *